United States Patent [19]

Wong et al.

[11] Patent Number: 4,972,830
[45] Date of Patent: Nov. 27, 1990

[54] INHALATION DEVICE AND METHOD

[75] Inventors: Gordon A. Wong; James I. C. Lee; Gary M. Peck, all of Sacramento, Calif.

[73] Assignee: Vortran Medical Technology, Inc., Sacramento, Calif.

[21] Appl. No.: 185,708

[22] Filed: Apr. 25, 1988

Related U.S. Application Data

[63] Continuation of Ser. No. 761,069, Jul. 31, 1985, abandoned.

[51] Int. Cl.$^5$ .......................................... A61M 11/00
[52] U.S. Cl. ........................... 128/200.21; 128/200.23
[58] Field of Search ................... 128/200.14, 200.18, 128/200.21, 200.23, 203.15, 203.12; 239/102, 338, 371, 403–434.5, DIG. 20, DIG. 23

[56] References Cited

U.S. PATENT DOCUMENTS

| | | | |
|---|---|---|---|
| 2,869,188 | 1/1959 | Cameto | 128/200.21 |
| 3,652,015 | 3/1972 | Beall | 239/338 |
| 3,848,807 | 11/1974 | Partida | 239/290 |
| 4,116,387 | 9/1978 | Kremer, Jr. et al. | 239/338 |
| 4,175,706 | 11/1979 | Gerstmann | 239/434.5 |
| 4,228,795 | 10/1980 | Babington | 128/200.22 |
| 4,241,877 | 12/1980 | Hughes | 239/405 |
| 4,267,974 | 5/1981 | Kienholz et al. | 239/74 |
| 4,284,590 | 8/1981 | DeBoer, Jr. et al. | 239/338 |
| 4,301,970 | 11/1981 | Craighero | 239/338 |
| 4,376,514 | 3/1983 | Coffee | 239/690 |
| 4,453,542 | 6/1984 | Hughes | 128/200.21 |
| 4,461,425 | 7/1984 | Miller | 128/200.21 |
| 4,484,577 | 11/1984 | Saekner et al. | 128/200.23 |
| 4,555,059 | 11/1985 | Collins et al. | 239/434.5 |
| 4,690,332 | 9/1987 | Hughes | 239/338 |

FOREIGN PATENT DOCUMENTS

| | | | |
|---|---|---|---|
| 84304805.9 | 7/1984 | European Pat. Off. | |
| 474904 | 7/1914 | France | |
| 3062 | 2/1912 | United Kingdom | 128/200.21 |
| 11930 | 6/1965 | United Kingdom | 128/200.21 |

OTHER PUBLICATIONS

Copy of Vortran Corporation PCT/US84/01517 (International Publication No. WO86/01730).

Primary Examiner—Randall L. Green
Assistant Examiner—K. M. Reichle
Attorney, Agent, or Firm—Limbach, Limbach & Sutton

[57] ABSTRACT

A device is disclosed for dispersing a fluid supplied from an external source having a feed supply. An inlet accepts a fluid from the feed supply for passing the fluid through an outer perimeter of the device in a downstream direction and has an axes contained in a plane. An outlet is provided downstream from the inlet for allowing the fluid to exit. A bluff body is positioned between the inlet and the outlet and has an axes contained in a plane perpendicular to the inlet axes plane. At least one passageway internal to the outer perimeter and external and extending downstream from the outlet for passing a second fluid is provided.

17 Claims, 4 Drawing Sheets

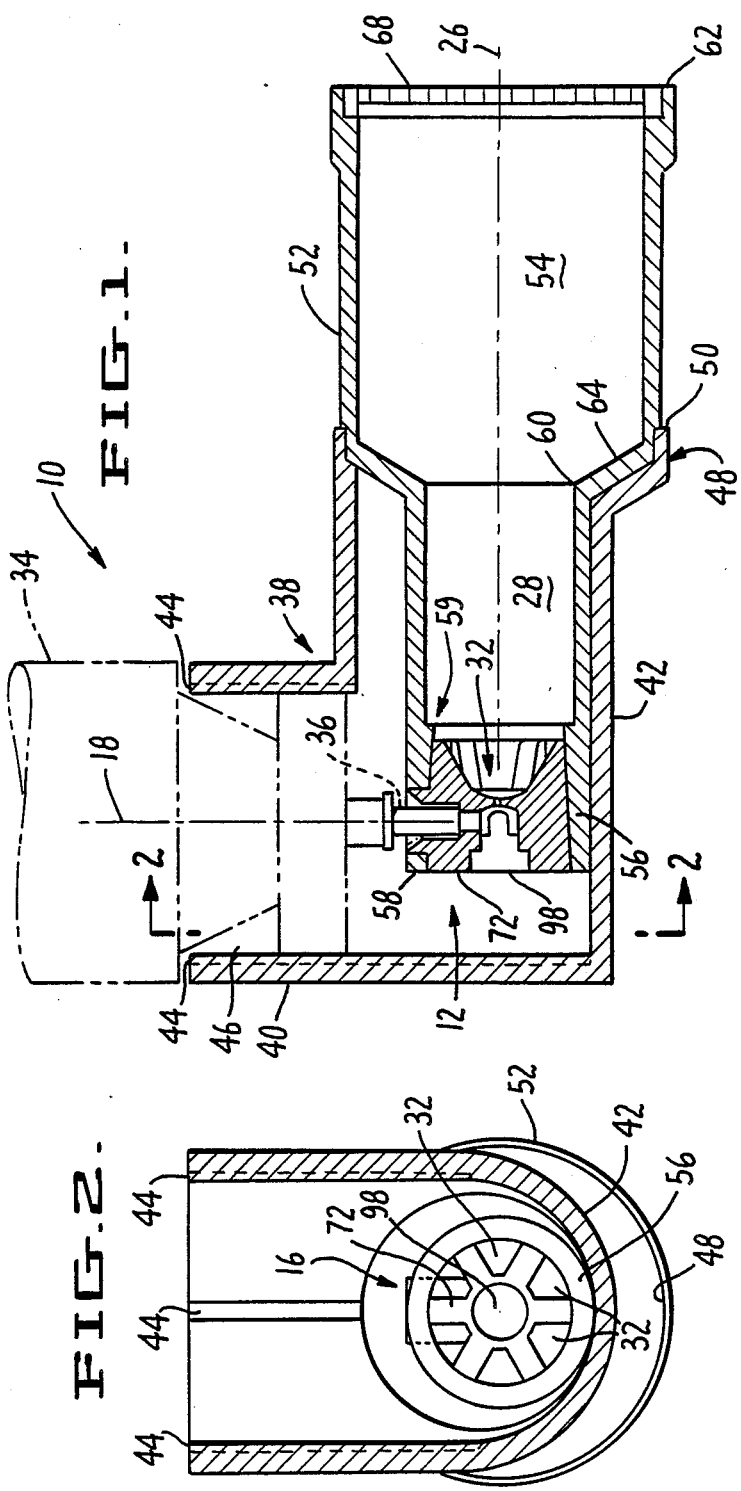

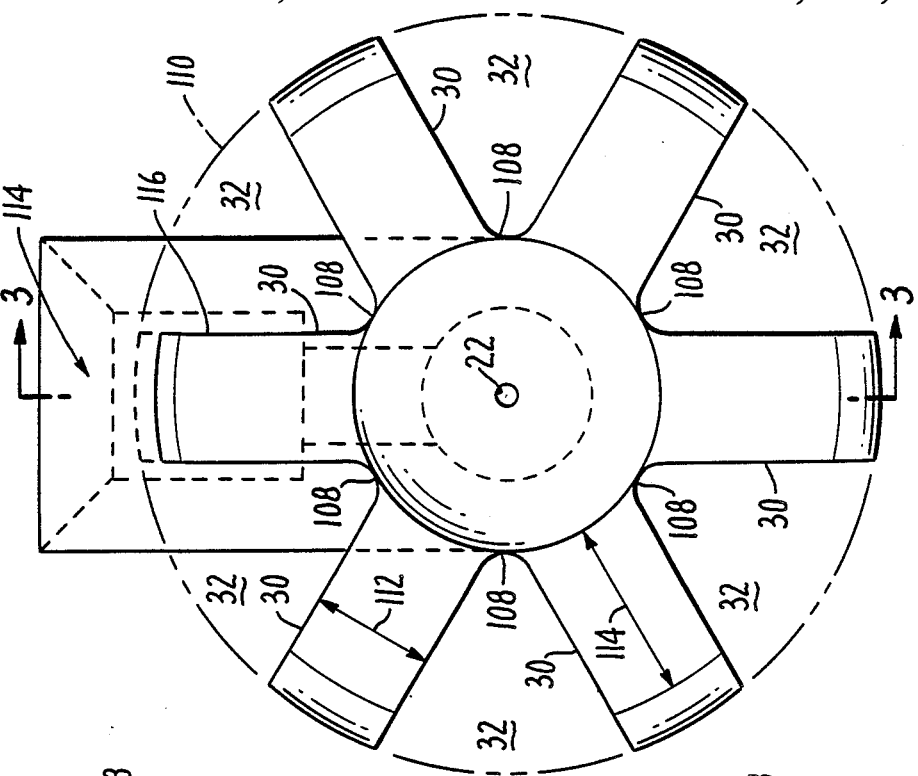
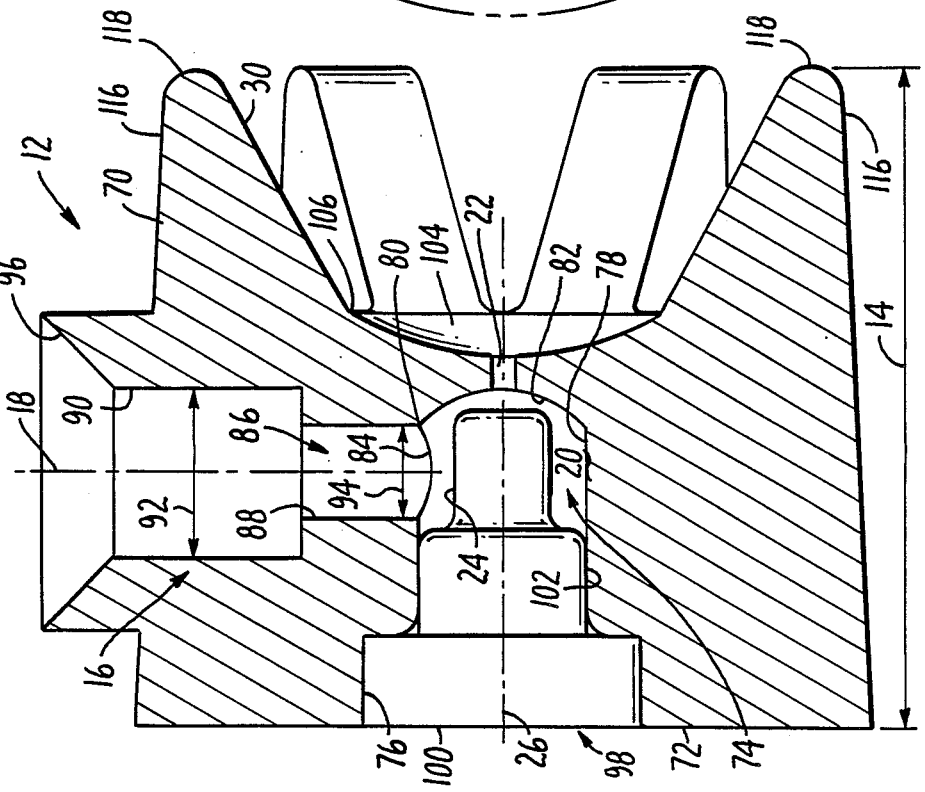

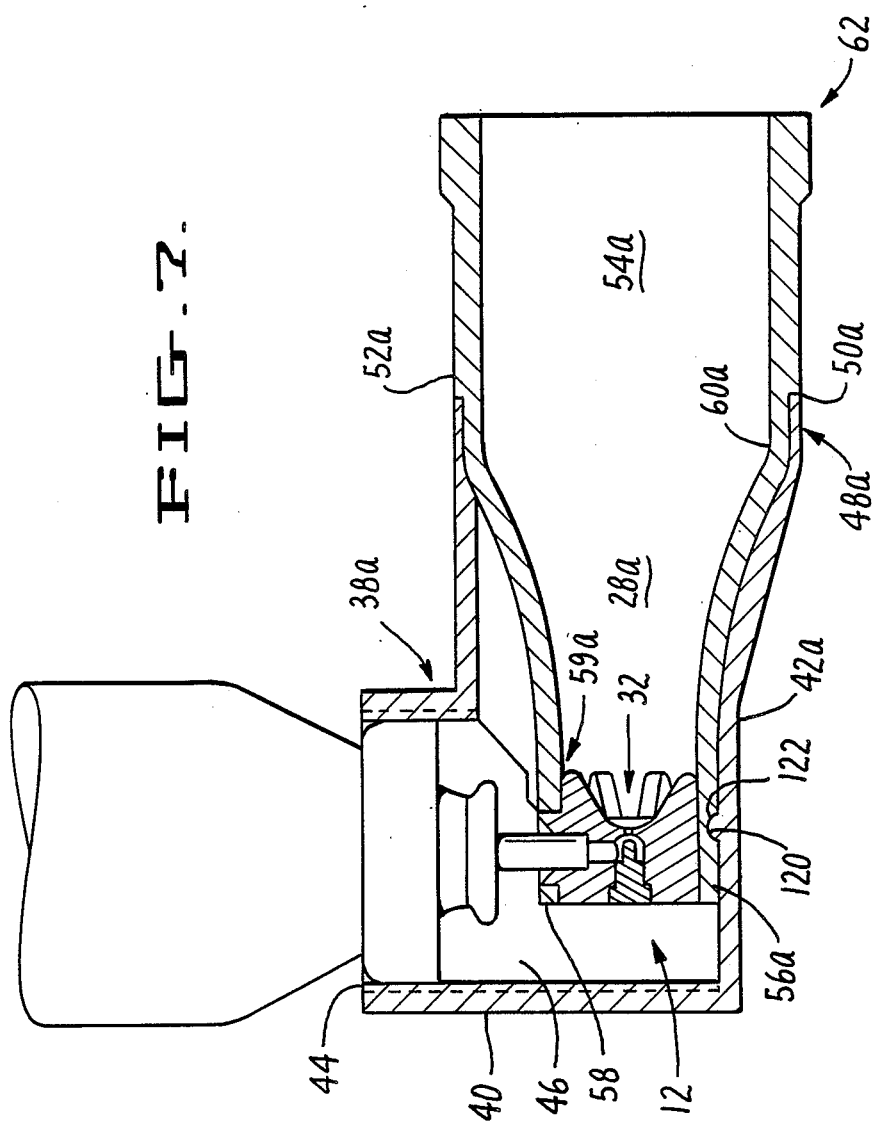

INHALATION DEVICE AND METHOD

This is a continuation of application Ser. No. 761,069, filed July 31,1985 now abandoned.

FIELD OF THE INVENTION

This invention relates to applicators for medicants and, more specifically, to inhalers.

BACKGROUND

Devices for creating medicated aerosol using propellant and medication inside a canister are widely used. Although many medications for asthma are delivered by these devices, the wide range of particle size produced along with significant forward velocity results in discomfort and impaction in the patient's oropharynx. Many attempts have been made to decrease velocity and impaction by the use of "spacers". Spacers are straight tubes or bags that are attached to the aerosol device in an attempt to provide uniform particle size with reduced velocity and impaction. Collapsible bags have also been used. The current spacers are cumbersome and have not found wide-spread patient acceptance. However, clinical studies have shown spacers to be helpful in improving delivery of drugs to patients having difficulty coordinating the high velocity of the aerosol with inhalation. Increased retention of the aerosol medication has been a problem with these devices. Without spacers, the delivery of the aerosol is uncomfortable to patients because of the cooler temperature associated with the liquified propellant and medication.

U.S. Pat. No. 4,241,877 to Hughes shows a vortex generating device in FIGS. 5A, 5B, and 6, wherein a gas and a liquid pass into a flow passage together from an inlet. The mixture flows about a rod and forms vortices thereabout and enters a bore along a portion of the rod after which the mixture exits the device through a constricted bore to a semispherical diverging outlet. The liquid is partially atomized as it leaves the bore in the inlet and becomes fully atomized as it leaves the semispherical diverging outlet in a vortical gas stream. A device is also shown where a gas and liquid under pressure are supplied together through an inlet member to a transversely extending rod for formation of vortices. The vortices flow in a direction coaxial with the rod to a constricted outlet bore and to a semispherical diverging outlet. The vortices also flow along auxiliary passages toward the constricted bore portion to combine with the previously-mentioned coaxial flowing vortices.

The Hughes '877 device is suitable for relatively high mass flow rates, but would not be suitable for use with the propellant-charged canisters containing a relatively low propellant-to-medication liquid ratio. With such canisters, it is desirable to minimize the proportion of propellant in each dose and maximize the vortical action of the mixture while it flows through the transducer. Furthermore, it would be difficult and expensive to manufacture a device as indicated in the Hughes '877 patent and still provide the aerosol production capabilities required in conjunction with the propellant-charged canister.

The inhalation device and method using vortex generating technology and combining it with entrainment on demand has resulted in a device capable of producing uniform particle size, comfortable temperature and without impaction. The reduced velocity will allow patients to easily coordinate actuations of the device with inhalation of the medicine. This will increase the amount of drug delivered to the lower respiratory tract and appropriate receptor sites instead of depositing in the oropharynx.

SUMMARY OF THE INVENTION

In the present invention, a device for dispersing a fluid from an external source having feed means comprises an inlet. The inlet accepts the fluid from the feed means and passes the fluid through an outer perimeter of the device in a downstream direction and has an axis contained in a plane. An outlet is provided in the device downstream from the inlet for allowing the fluid to exit the device. A bluff body is positioned between the inlet and the outlet and has an axis contained in a plane perpendicular to the inlet axis plane. Means is provided for defining at least one passageway internal to the outer perimeter and external to and extending downstream from the outlet for passing a second fluid. This arrangement provides a dispersed fluid from input fluid having a low flow rate and is notably efficient. The device allows for entrainment of a second fluid from a source other than the external source and the flow passages for the first fluid. For example, the second fluid may be the ambient air. This enhances dispersion and mixing of the first fluid. The device is also relatively easy to manufacture and assemble.

Disclosure is also made of an apparatus for applying medication as an aerosol comprising a transducer having a first fluid supply, a first chamber downstream from the first fluid supply, an outlet downstream from the first chamber and a bluff body between the inlet and the outlet. A second chamber is positioned downstream from the outlet and means is positioned between the first chamber and the transducer, and extending a length of the transducer, for defining at least one passageway for passing a second fluid. This arrangement provides an aerosol delivered at a very small or negligible velocity thereby minimizing impact of the aerosol on the patient. The device provides a mist having droplets which are uniform in size regardless of the variation in range of pressure provided through the liquified propellant in a propellant canister. This is also the case regardless of the amount medication atomized. The second chamber is approximately one-fourth the size of the spacer of the prior devices and is used to create the low velocity aerosol. The majority of droplets produced by the device are one-to-three microns which are important for delivery to the lower respiratory tract and receptor sites.

BRIEF DESCRIPTION OF THE DRAWINGS

FIG. 1 is a schematic and side sectional view of an apparatus for dispersing fluid in combination with a tube and sleeve forming an apparatus for applying medication as an aerosol;

FIG. 2 is a schematic and partial side section of the apparatus of FIG. 1 showing the device with means for forming a passageway;

FIG. 3 is a schematic and side section of a transducer for the apparatus shown in FIG. 1 and showing flow passages through the transducer;

FIG. 4 is a schematic and side elevation view of the transducer of FIG. 3;

FIG. 7 is a schematic and partial side section view of an additional embodiment of an apparatus similar to that shown in FIG. 1.

DETAILED DESCRIPTION

Figure 5:
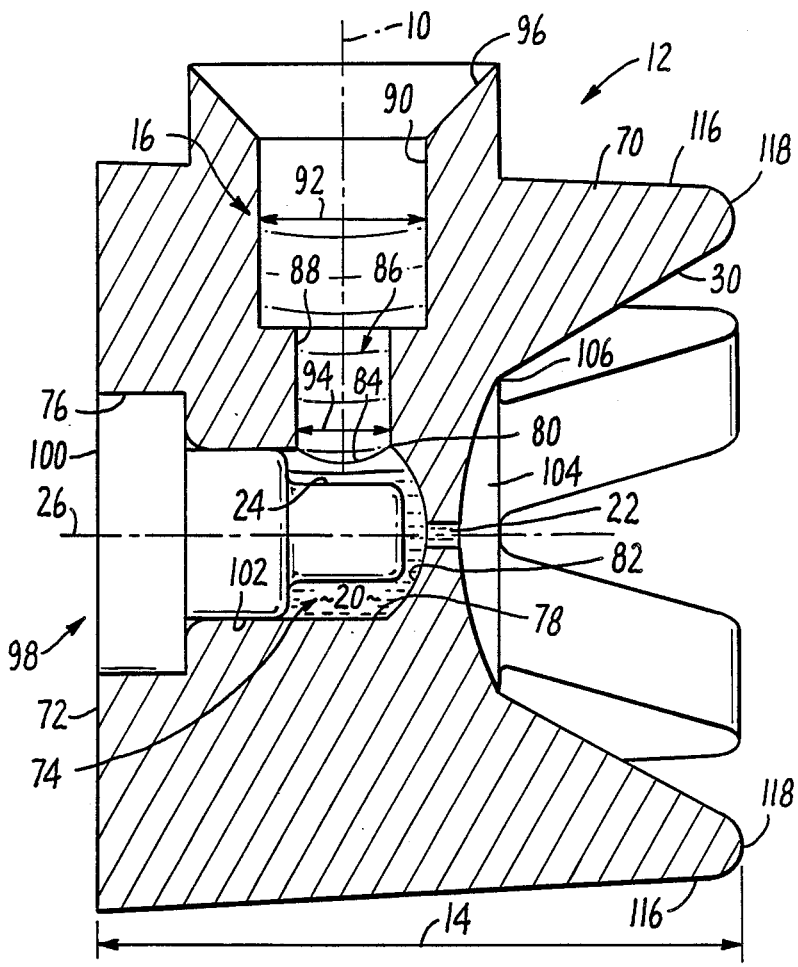
FIG. 5 is a schematic and sidesection of the device similar to that shown in FIG. 3 showing the pattern of fluid flow in the device.
Figure 6:
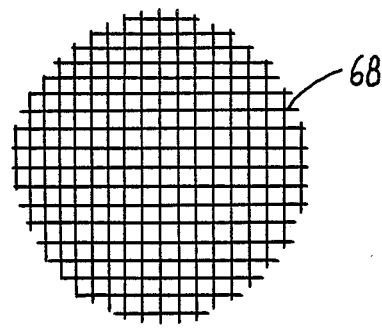
FIG. 6 is a schematic and plan view of a resonant screen for use in the apparatus of FIG. 1.

The description herein of the apparatus and its use includes a description of the method for applying medication as an aerosol. Reference is made to International Publication No. WO 85/02345 June 6, 1985 oriented to a Single Inlet Prepackaged Inhaler and to U.S. Pat. No. 4,241,877, oriented to a Stable Vortex Generating Device. The material of these publications are incorporated herein.

FIG. 1 of the present invention shows an apparatus in the form of an inhaler 10 for applying medication as an aerosol to a patient. A transducer 12, shown in detail in FIG. 3, includes a length 14 and has means in the form of an inlet 16 for supplying a first fluid (not shown). The inlet has a first axis 18. A first chamber 20 opens from the inlet 16 at a portion downstream from the inlet oriented vertically, as shown in FIG. 3. (Directional terms used herein such as vertical, horizontal and upward are intended to be used for reference to the drawings only and are not limitation on the structure or function of the device.) An outlet 22 is positioned downstream from the first chamber 20. A bluff body 24 is positioned between the inlet 16 and the outlet 22 and has an axis 26 contained in a plane (not shown) perpendicular to a plane (not shown) containing the first or inlet axis 18. A second chamber 28 in the form of an expansion chamber is positioned downstream from the outlet for expanding the fluid. Means in the form of spokes 30 for defining at least one passageway 32 is positioned between the second chamber 28 and the transducer 12 for passing a second fluid, such as air. The spokes 30 extend the length 14 of the transducer.

Consider now the apparatus in detail with respect to the drawings. The inhaler 10 is adapted to accept a container 34 of a mixture of propellant and medication (not shown). A nozzle 36 extends from one end of the container for dispensing the propellant and medication under pressure. The container has a structure and function similar to that of metered-dose containers generally known in the art.

The inhaler 10 includes a sleeve 38 for holding the container and for providing a support structure for the remainder of the apparatus. The sleeve has a vertical leg 40 and a horizontal leg 42 wherein the vertical leg is adapted to accept the nozzle end of the container 34. The vertical leg 40 is substantially hollow and cylindrical in cross-section with a plurality of guide ridges 44 extending vertically and inwardly from the interior surface 46 of the vertical leg 40. The guide ridges support and retain the container 34 in a vertical position when placed in the inhaler 10.

In the embodiment of FIG. 1, the horizontal leg 42 of the sleeve 38 is tubular or substantially hollow cylindrical in transverse cross-section. The inside diameter of the horizontal leg has a diameter which is less than the inside diameter of the vertical leg of the sleeve. The terminal end 48 of the sleeve includes a lip 50 extending outwardly from the lower portion of the horizontal leg 42. The upper portion of the horizontal leg extends essentially horizontally to the terminal end 48. The sleeve 38 is dimensioned to accept, in the horizontal leg 42, a tube 52, to be described more fully below, containing the transducer 12. The sleeve 38 also provides for the intake of air between the container 34 and the walls of the vertical leg 40 to allow entrainment of air through the passageways 32 about the transducer 12.

The tube 52 supports and retains the transducer 12 and includes the second expansion chamber 28 and a third expansion chamber 54 for expanding the fluid. The tube and transducer partially fit inside the horizontal leg 42 of the sleeve 38. The outside dimensions of the tube 52 are largely dictated by the outside dimensional requirements of the transducer, the internal dimensional requirements of the second and third expansion chambers, and by the coupling required between the terminal end 48 and the tube 52.

The tube 52 includes a transducer mount 56 for enclosing and supporting the circumferential surface of the transducer at an upstream end of the tube. The transducer mount includes a keyslot 58 for accepting the inlet of the transducer. The interior wall of the transducer mount converges in a downstream direction from 0.467 inch to 0.427 inch to assist in focusing the flow of the incoming air from the upstream end of the transducer passageways and to more easily hold the transducer. The sleeve and tube are preferably formed of a medical grade plastic, but may also be made from other materials.

The second expansion chamber 28 begins at the downstream terminus 59 of the transducer mount 56 and extends in a downstream direction to the beginning of the third expansion chamber 54. The inside diameter of the second expansion chamber preferably increases from 0.467 inch at the extreme upstream end of the second chamber 28 to approximately 0.480 inch at the extreme downstream end. The length of the expansion chamber 28 is preferably 0.745 inches. The third expansion chamber 54 extends from the end 60 of the second expansion chamber to the downstream end 62 of the tube. The third expansion chamber begins with a diverging conical portion 64 having an inside surface extending outwardly and downstream at an angle of approximately 60° with respect to a horizontal axis 26. The inside surface of the remainder of the third expansion chamber is substantially cylindrical in crossection and preferably comprises an inside diameter of approximately 0.940 inch. The length of the third expansion chamber is preferably 1.274 inches from the end 60 of the first expansion chamber to the downstream end 62 of the tube.

In the embodiment of FIG. 1, the tube includes means comprising apertures having lattice pieces in the form of screen 68 mounted to the downstream end 62 of the tube for setting up a standing wave pattern (not shown) in the expansion chambers, to assist in uniformly dispersing particles in the vortex and for serving as a drag brake to break up the remaining particles in the vortex. The screen is preferably formed of a nylon lattice having an extreme diameter of 0.980 inch and a square lattice opening dimension of 0.060 inch×0.060 inch. Each lattice member is preferably 0.012 inch across the face and 0.024 inch from one face of the screen to the other. In the preferred embodiment of the invention, the screen 68 is omitted.

The transducer will now be considered in more detail with respect to FIGS. 2-4. The transducer 12 has a transducer body 70. The transducer body includes a flat circular base 72 having formed therein a substantially cylindrical recess 74 and a counterbore 76.

The cylindrical recess 74 is formed by a cylindrical chamber wall 78 extending from the bottom of the counter-bore 76 to a rim 80 in the chamber wall. The cylindrical recess is closed at the bottom thereof by a second chamber wall 82 constituting a portion of a sphere. The surface is curved to present minimum obstruction to flow once the vortices are created. The end of the bluff body is curved for the same purpose.

An aperture 84 is formed in the cylindrical chamber wall 78 and is adjacent the rim 80 of the chamber wall. The aperture forms an opening for the inlet 16 to the first chamber 20. The inlet includes an inlet restriction 86 having a cylindrical wall 88 extending to the aperture 84.

The inlet further includes a counterbore 90 having a circular cross-section and a diameter 92 greater than the diameter 94 of the aperture. The counterbore 90 accepts the nozzle 36 of the medication container 34. The inlet also includes a conically shaped surface 96 converging to the counterbore 90.

The first chamber 20 terminates at a downstream portion in the outlet 22. The outlet is substantially a pinhole having a circular transverse crossection.

A plug 98 is adapted to be placed in the cylindrical recess 74 and includes a round, flat head 100 to mate with the counterbore 76. The plug includes a reduced shaft 102 adjacent the head 100 for mating with the chamber wall 78. The reduced shaft serves to close off the cylindrical recess to form the first chamber 20. The bluff body 24 is a further reduced portion adjacent the reduced shaft extending into the first chamber 20 and past a plane defined by the rim 80 of the second chamber wall. Therefore, the end of the body 24 extends to a point between two parallel planes (not shown), the first defined by the rim 80 and the second defined by the upstream portion of outlet 22. The plug, including the head, reduced shaft and bluff body are oriented about the axis 26, which is perpendicular to axis 18. The bluff body extends across, in spaced apart relation with, the aperture 84.

The outlet 22 terminates in an expansion surface 104 defining a portion of a sphere and is curved so that the flow from the outlet is as free from disruption as possible. This helps to minimize deposition fluid on the transducer and maximize the proportion of medication delivered. The expansion surface extends downstream to a portion defining a rim 106.

The transducer also includes a plurality of spokes 30 defining a plurality of passageways 32. As shown in FIGS. 2 and 4, the spokes extend radially outward from an outer surface 108 of the transducer to an outer perimeter 110. The spokes 30 and therefore the transducer are supported by the transducer mount 56, shown in FIG. 1. In the preferred embodiment, there are six spokes oriented equidistant about the outer surface of the transducer. Each spoke has a width 112 from one side to the other, on opposite sides of a respective axis 114. Adjacent axes are preferably spaced approximately 60" apart. A top vertical spoke 116 is preferably oriented along a radius defined by the first axis 118, about which the inlet 16 is oriented. As shown in FIG. 3, the top vertical spoke extends in an upstream and a downstream direction from the inlet 16. The remaining spokes extend from the flat circular base 72 of the transducer substantially the length 14 of the transducer. Each spoke terminates in a preferably rounded end 118 at the downstream terminus of the transducer. Additionally, each spoke has a corresponding diametrically opposite spoke, forming a pair defining the perimeter of the transducer. The diameter of the perimeter of the transducer decreases in the downstream direction from the base 72 to the rounded ends 118 for engaging the transducer mount 56 in the tube 52.

The transducer and plug are preferably made of medical grade plastic. However, as with the sleeve and tube, it is possible that the transducer and plug be made from other materials. The dimensions of the transducer and plug are as follows: the diameter of the cylindrical recess 74 is 0.110 inch; the diameter of the aperture 84 is 0.060 inch; the diameter of the counterbore 90 is 0.108 inch; the extreme diameter of the conically shaped surface 96 is 0.196 inch; the length of the counterbore 90 conically shaped surface 96 is 0.170 inch; the distance from the axis 26 to the extreme end of conically shaped surface 96 is 0.294 inch; The height of the head 100 of plug 98 is 0.060 inch; the combined length of the reduced shaft 102 and bluff body 24 is 0.140 inch; the distance from the face 72 to the upstream portion of outlet 22 is 0.0213 inch; the length of outlet 22 is 0.020 inch; the inside diameter of outlet 22 ranges from 0.014 to 0.022 inch; the angle with which the downstream spoke surface, defining a portion of a cone, mates with the horizontal is 30°; the length 14 is 0.415 inch; the diameter of the expansion surface 104 is 0.200; the radius of the outer perimeter 110 is 0.234 inch; the shortest radius of the perimeter of the transducer is 0.218 inch; the width 112 is 0.080 inch; and the radius of curvature of the expansion surface 104 is 0.218.

In a preferred embodiment of FIG. 7 the Inhaler 10 is similar to the Inhaler 10 of FIG. 1. Elements in FIG. 7 identical to those of FIG. 1 are labeled with the same reference numerals and have the same structure and function The inhaler has a sleeve 38 having a horizontal leg *42a*. The horizontal leg *42a* of the sleeve is hollow and substantially circular in transverse crossection. The terminal end *48a* of the horizontal leg includes a lip *50a* extending outwardly from the lower portion of the horizontal leg. The lower portion extends substantially horizontally from the left side of the sleeve to a point midway along the sleeve and then downwardly in the right hand direction to the terminal end *48a*. The upper portion of the sleeve extends substantially horizontally from the vertical leg to the terminal end *48a*. With this configuration, the horizontal leg of the sleeve has a circular transverse cross-section of increasing diameter from left to right beginning at the approximate midportion of the horizontal leg. The remainder of the surface of the horizontal leg is so formed to provide a smooth surface from the top portion of the horizontal leg to the bottom portion and from left to right. The terminal end *48a* is also circular in cross-section for accepting the tube *52a* described more fully below.

The internal dimensions of the sleeve are configured to accept and hold the tube *52a*. Specifically, a ridge 120 extends into the interior of the sleeve at a point to the left of the midportion for engaging a groove 122 in the tube *52a*. The thickness of the wall of the horizontal leg is substantially constant between the left end and the midportion of the sleeve. Thereafter, the outside surface follows a relatively straight path outwardly and to the right while the inside surface follows a curved path whereby the thickness of the wall increases and then decreases toward the terminal end *48a*. At any given point on the lower portion of the horizontal leg, the wall thickness is a maximum at the lower portion of the horizontal leg and decreases toward the upper portion of the horizontal leg.

The tube 52a supports and retains the transducer 12 and includes the second expansion chamber 28a and the third expansion chamber 54a for expanding and decreasing the forward velocity of the fluid. The tube and transducer partially fit inside the horizontal leg 42a of the sleeve 38a. The outside dimensions of the tube 52a are largely dictated by the outside dimensional requirements of the transducer, the internal dimensional requirements of the second and third expansion chambers and by the coupling required between the terminal end 48a and the tube 52a.

The tube includes a transducer mount 56a for enclosing and supporting the circumferential surface of the transducer at an upstream end of the tube. The transducer mount includes a keyslot 58 for accepting the inlet of the transducer. The transducer is substantially the same as described with respect to FIGS. 1–6. The interior wall of the transducer mount converges in a downstream direction to assist in focusing the flow of the incoming air from the upstream end of the transducer passageways to more easily hold the transducer.

The second expansion chamber 28a begins at the downstream terminus 59a of the transducer mount and extends in a downstream direction to the end 60a of the second expansion chamber and the beginning of the third expansion chamber. The walls of the second expansion chamber 28 preferably define a surface in the form of a portion of a hyperboloid of one sheet. As a result, the transverse cross-sectional shape of the second expansion chamber is substantially circular and increases in diameter from left to right. The inside diameter of the second expansion chamber preferably increases from approximately 0.467 inch at the extreme upstream end to approximately 0.940 inch at the extreme downstream end 60a. This provides a radius of curvature of approximately two inches. The length of the second expansion chamber is preferably 0.995 inch.

The third expansion chamber 54a extends from the end 60a of the second expansion chamber to the downstream end 62 of the tube. The third expansion chamber is substantially circular in transverse crossection having a substantially constant inside diameter of approximately 0.940 inch from beginning to end. The length of the third expansion chamber is preferably 1.088 inch.

The transducer 12 is substantially the same as described above with respect to FIGS. 2–4.

The operation of the apparatus will now be described with respect to FIGS. 1–6. The inhaler 10 is assembled as would be apparent to one skilled in the art. A container 34 of a mixture of propellant, active medication and solvent is placed in an inverted fashion into the vertical leg of the sleeve 38. The outlet port of the nozzle 36 is then confluent with the inlet restriction 86 of the inlet 16. The staging chamber of the container 34 is filled with the appropriately metered dose of the mixture of propellant and medication. The container is then depressed relative to the counterbore 90 so that the nozzle is forced further into the mouth of the container. The mixture contained in the staging chamber is ejected under pressure of between 30 and 50 psi, depending upon the particular container being used. The volume of the staging chamber may be approximately 0.05 cubic centimeters so that the total volume of the mixture of propellant and medication is approximately 0.05 cubic centimeters. As discussed in the '877 patent, the phenomenon of "cold boiling" and/or the resultant atomization of the liquid in the propellant/solvent mixture may occur when the injected mixture is pressurized and then released into the inlet restriction of the inlet 16. Preferably, the ratio of the gas pressure to the ambient pressure is greater than the critical pressure ratio. For example, the pressure of the mixture in the container may be approximately 50 psi, gauge (psig). The propellant-to-liquid ratio may be typically 30:1 and the volume of output per dose may be 0.05 cubic centimeters.

As a result of the high propellant and liquid pressure, the flow of gas is supersonic as it enters the inlet restriction 86. The ejected fluid expands into the inlet. The fluid flows along the inlet without further significant change in volume or velocity until reaching the aperture 84, where the mixture is then injected into the first chamber 20. The mixture again goes through expansion into the chamber 20. The presence of the bluff body in front of the supersonic fluid gives rise to a standing shockwave as shown in FIG. 5. A very large number of vortices is thereby generated about the bluff body. The potential energy, i.e., static pressure, of the gas supplied to the inlet, is in effect, partly converted to kinetic energy—first as an increase in linear gas velocity, then as shock waves, and finally as vortices in the flow passage. The vortices are formed having axes generally parallel to the bluff body. It is estimated that the pressure at the bluff body is approximately 20–30 psig. It is estimated that the tiny vortices are formed at a rate of approximately 40,000–50,000 vortices per second. This is due to the high velocity of the flow and to the dimensional compactness of the apparatus. Formation of a maximum number of vortices per unit/time is preferred. The number of vortices generated by the device is proportional to the gas velocity and the drag area across which the gas flows and the requisite coeffecient of drag. Because of the pressure difference between the inlet and the outlet 2, there is a pressure gradient toward the second chamber wall 82, along the outlet 22 and to the expansion surface 104. The individual vortices are focused along the second chamber wall toward the outlet 22. The spinning vortices are then compressed and forced by the pressure gradient into the outlet, followed by sudden expansion into a single large vortex (not shown).

The vortex activity from the bluff body to the final large vortex produces atomization of the liquid fraction in the liquid-propellant mixture so that medication contained in the liquid fraction is atomized into a mist substantially containing 1 to 3 micron-sized monodispersed droplets for entering the first expansion chamber 30. It was found that one massive vortex was formed by impinging the vortices on a rod and letting them escape through an annular chamber.

The single large exiting vortex is comprised of fluid flowing at supersonic velocity due to the compression of the vortices flowing through the orifice and due to the pressure difference across the orifice being greater than the critical pressure. The dose mixture went through a first supersonic flow regime, followed by expansion and creation of vortices. The vortices were then focused and forced out the outlet to the downstream side of the orifice where the pressure is approximately atmospheric. The exiting vortex represents a conversion of a substantial amount of static energy to dynamic energy. The vortex is spinning about the axis 26.

The single vortex includes a negative pressure at the center thereof due to the pressure differential across the orifice being greater or equal to the critical pressure ratio. It is found that there is enhanced atomization with this configuration.

The passageways allow entrainment of external air by the negative pressure zone and the single exiting vortex. Entrainment occurs along the passageways and mixing of the external air with the fluid from the outlet 22 occurs between the expansion surface 104 and a downstream portion of the inhaler. This has been found to decrease the rate of retention of the medication in the inhaler.

The second expansion chamber 28 provides for expansion of the vortex, thereby reducing the velocity and, therefore mean free path of the individual medication particles and provides an area for confining the atomized vapor. The expansion and slowing of the particles in combination with the entrainment inhibits condensation or the individual particles and deposition of the particles along the chamber wall. The forward velocity of the particles is transferred to increased random motion of the individual particles. Additionally, it is believed that further atomization of the particles may occur to a limited extent.

As the vortex continues to the third expansion chamber 54, a like process occurs, without entrainment, whereby the forward velocity of the individual particles is further decreased and the vapor vortex is further expanded due to the increased crossectional area of the third expansion chamber. The effect of the increase in crossectional area on the vortex is the same as that from the expansion in the second expansion chamber. The third expansion chamber assists in storing the vapor in the vortex, slows the vortex in its forward movement and allows creation of greater vorticity when the fluid reaches the resonant screen, to be described more fully below.

The fluid in the vortex is then impacted on the resonant screen with several resulting effects. The screen resonates to set up a standing wave pattern in the expansion chambers to assist in uniformly dispersing particles in the vortex in the second expansion chamber. It also serves as a drag brake to break up the remaining particles in the vortex. This is enchanced by the fact that a force of drag on the fluid flow is more significant than the force due to the forward momentum of the fluid. Therefore, the effects due to the drag force predominate over the effect due to forward flow of the fluid. Additionally, as the vortex impacts the resonant screen, individual spinning vortices are produced in each square of the resonant screen due to the appearance to the fluid of individual bluff bodies oriented perpendicular to each other. There is also evidence of some vibration in the resonant screen. The position of the screen relative to the transducer and to the expansion chambers maximizes resonant effect and standing wave action, and also the production of the desired particle size, even after the fluid slows down in the expansion chambers. The final result, after impingement of the fluid on the resonant screen, is a soft, "warm", low-velocity mist or vapor to be inhaled by a patient. The mist will have minimal, if any, impact on the air passageways in the patient's mouth and lungs as the vapor is inhaled. The apparent temperature of the aerosol is more acceptable to the patient also.

The operation of the inhaler of FIG. 7 is substantially the same as that described with respect to FIGS. 1-6 except for the effect of the second expansion chamber 28 and the absence of the resonant screen. When the single exiting vortex and the entrained fluid enter the second expansion chamber, expansion of the mixture takes place gradually over the length of the second expansion chamber. Expansion takes place along the entire length of the second expansion chamber and it is believed that the configuration of the single existing vortex is maintained better than with the tube of FIG. 1 during the transition between the second and third expansion chambers. The resonant screen is omitted from the end of the tube to minimize deposition of medication of the lattice of the resonant screen.

The results obtained in the transducer combined with the expansion chambers are reproducable for any medication delivery canister presently marketed. The same output is still effected. When the inhaler is manufactured in a plastic molding process, the inhaler may be disposable after completion of a medication regimen from one or more medication canisters. The inhaler is easy to reliably manufacture and easily assembled with press-fit parts. The inhaler is compact and convenient to hold and carry Entrainment of external air is provided to minimize medicine deposition in the expansion chamber and improve delivery to the patient.

It should be noted that the above are preferred configurations but others are foreseeable. The embodiments of the invention are only considered to be preferred and illustrative of the inventive concept; the scope of the invention is not to be restricted to such embodiments. Various and numerous other arrangements be devised by one skilled in the art without departing from the spirit and scope of the invention.

What is claimed is:

1. An apparatus for dispersing a first fluid supplied from an external source entrained with a second fluid, the apparatus comprising:

a transducer body having a first inlet, a first chamber, a bluff body in said first chamber, a length and an outlet;

said first inlet having means for receiving the first fluid from the external source and an inlet axis, said first inlet being connected to said first chamber for passing the first fluid thereto;

said bluff body having a bluff axis, which is substantially perpendicular to said inlet axis, and being positioned to intersect said inlet axis such that the first fluid from the first inlet impinges on said bluff body, said bluff body terminating at a bluff body end which is located upstream of said transducer body outlet;

said length being defined in a direction substantially parallel to said bluff axis;

said outlet having an outlet axis which is substantially parallel to said bluff axis, and being connected to said first chamber for receiving the first fluid from said first chamber, said outlet terminating with a substantially hemispherically-shaped expansion surface which increases diametrically in a direction towards the exterior of the transducer body;

a plurality of spaced apart spokes extending from the exterior surface of said transducer body, said spokes having a length defined in a direction substantially parallel to said bluff axis and defining a gap, extending in the lengthwise direction, between adjacent ones thereof, at least two adjacent spokes extending, in the lengthwise direction, the entire length of the transducer body and the gap defined therebetween having means for fluidically connecting with the second fluid; and means for receiving the first fluid from the expansion surface, allowing entrainment of the second fluid through the gap between the at least two spokes by the first fluid, mixing of the first and second fluids and dispersing of the mixture, said receiving means including a second chamber.

2. The apparatus of claim 1, wherein said second chamber includes:
a substantially cylindrically-shaped surface having a first end fluidically connected to said expansion surface and the gap between said at least two spokes, said first end for receiving the first fluid and the second fluid and a second end, larger than said first end and positioned downstream therefrom, for dispersing the first and second fluids.

3. An inhaling apparatus comprising:
a container containing a first fluid which is a mixture of a propellant and a medicament, said container having discharge means for discharging said first fluid therefrom;
a transducer body having a first inlet, a first chamber, a bluff body in said first chamber, a length and an outlet;
said first inlet having means for receiving the first fluid from the container and an inlet axis, said first inlet being connected to said first chamber for passing the first fluid thereto;
said bluff body having a bluff axis, which is substantially perpendicular to said inlet axis, and being positioned to intersect said inlet axis such that the first fluid from the first inlet impinges on said bluff body end which is located upstream of said transducer body outlet;
said length being defined in a direction substantially parallel to said bluff axis;
said outlet having an outlet axis which is substantially parallel to said bluff axis, and being connected to said first chamber for receiving the first fluid from said first chamber, said outlet terminating with a substantially hemispherically-shaped expansion surface which increases diametrically in a direction towards the exterior of the transducer body;
a plurality of spaced apart spokes extending from the exterior surface of said transducer body, said spokes having a length defined in a direction substantially parallel to said bluff axis and defining a gap, extending in the lengthwise direction, between adjacent ones thereof, at least two adjacent spokes extending, in the lengthwise direction, the entire length of the transducer body and the gap defined therebetween having means for fluidically connecting with ambient air; and
means for receiving the first fluid from the expansion surface, allowing entrainment of ambient air through the gap between the at least two spokes by the first fluid, mixing of the first fluid and ambient air and dispersing of the mixture to the inhalation passages of a user, said receiving means including a second chamber.

4. The apparatus of claim 3, wherein said second chamber includes:
a substantially cylindrically-shaped surface having a first end fluidically connected to said expansion surface and the gap between said at least two spokes, said first end for receiving the first fluid and the ambient air and an inhalation port positioned downstream from said first end for dispersing the first fluid and the ambient air.

5. An inhaling apparatus comprising:
a container containing a first propellant medicament fluid, said container having a discharge means for discharging said first fluid therefrom;
a transducer body having a first inlet, a first chamber, a bluff body in said first chamber, a length and an outlet;
said first inlet having means for receiving the first fluid from the container and an inlet axis, said first inlet being connected to said first chamber for passing the first fluid thereto;
said bluff body having a bluff axis, which is substantially perpendicular to said inlet axis, and being positioned to intersect said inlet axis such that the first fluid from the first inlet impinges on said bluff body, said bluff body terminating at a bluff body end which is located upstream of said transducer body outlet;
said length being defined in a direction substantially parallel to said bluff axis;
said outlet having an outlet axis which is substantially parallel to said bluff axis, and being connected to said first chamber for receiving the first fluid from said first chamber;
means for permitting entrainment of a second fluid, said entraining means includes a port exterior and lateral of said transducer body and having means for fluidically connecting with a second fluid; and
means for receiving the first fluid from said outlet, allowing entrainment of the second fluid through the port by the first fluid, mixing of the first and second fluids and dispersing of the mixture, to the inhalation passage of a user said receiving means including a second chamber.

6. The apparatus of claim 5, wherein bluff body comprises a rod having a central axis, said central axis is said bluff axis.

7. The apparatus of claim 5, wherein said outlet terminates with a substantially hemispherically-shaped expansion surface which increases diametrically in a direction towards the exterior of the transducer body.

8. The apparatus of claim 7, wherein said entraining means further includes a plurality of spaced apart spokes extending from the exterior surface of said transducer body, said spokes having a length defined in a direction substantially parallel to said bluff axis and defining a gap extending, in the lengthwise direction, between adjacent ones thereof.

9. The apparatus of claim 8, wherein at least two adjacent spokes extending, in the lengthwise direction, the entire length of the transducer body and the gap being defined therebetween.

10. The apparatus of claim 9, wherein the port is the gap defined between the at least two adjacent spokes.

11. The apparatus of claim 5, wherein said second chamber includes:
a substantially cylindrically-shaped surface having a first end fluidically connected to said outlet and the port, said first end for receiving the first fluid and the second fluid and a second end, larger than said first end and positioned downstream therefrom, for dispersing the first and second fluids.

12. An apparatus for dispersing a first fluid supplied from an external source entrained with a second fluid, the apparatus comprising:
a transducer body having a first inlet, a first chamber, a bluff body in said first chamber, and an outlet;

said first inlet having means for receiving the first fluid from the external source and an inlet axis, said first inlet being connected to said first chamber for passing the first fluid thereto;

said bluff body having a bluff axis, which is substantially perpendicular to said inlet axis, and being positioned to intersect said inlet axis such that the first fluid from the first inlet impinges on said bluff body, said bluff body terminating at a bluff body end which is located upstream of said transducer body outlet;

said outlet having an outlet axis which is substantially parallel to said bluff axis, and being connected to said first chamber for receiving the first fluid from said first chamber;

means for permitting entrainment of the second fluid, said entraining means includes a port exterior and lateral of said transducer body and having means for fluidically connecting with the second fluid; and means for receiving the first fluid from said outlet, allowing entrainment of the second fluid through the port by the first fluid, mixing of the first and second fluids and dispersing of the mixture, said receiving means including a second chamber.

13. The apparatus of claim 12 wherein said outlet terminates with a substantially hemispherically shaped expansion surface which increases diametrically in a direction towards the exterior of the transducer body; and a substantially cylindrically-shaped surface having a first end fluidically-connected to said outlet and the port, said first end for receiving the first fluid and the second fluid and a second end, larger than said first end and positioned downstream therefrom, for dispersing the first and second fluids.

14. The apparatus of claim 13 wherein said entraining means further includes a plurality of spaced apart spokes extending from the exterior surface of said transducer body, said spokes having a length defined in a direction substantially parallel to said bluff axis and defining a gap extending, in the lengthwise direction, between adjacent ones thereof; and wherein said transducer body has a length, which is substantially parallel to said bluff axis, at least two adjacent spokes extending, in the lengthwise direction, the entire length of the transducer body and the gap being defined therebetween.

15. The apparatus of claim 14 wherein the port is the gap defined between the at least two adjacent spokes.

16. The apparatus of claim 12 wherein said bluff body comprises a rod having a central axis, said central axis is said bluff axis, and said bluff axis is substantially coaxial with said outlet axis.

17. The apparatus of claim 12 wherein said outlet axis is substantially co-axial with said bluff axis.

* * * * *